United States Patent [19]

Yalpani et al.

[11] Patent Number: 4,952,684
[45] Date of Patent: Aug. 28, 1990

[54] PROCESSES FOR THE PREPARATION OF AMIDES AND AMINES FROM A MATERIAL HAVING CARBOXYL-CONTAINING POLYSACCHARIDES AND PRODUCTS THEREFROM

[75] Inventors: Manssur Yalpani; Magdy M. Abdel-Malik, both of Kirkland, Canada

[73] Assignee: Domtar Inc., Montreal, Canada

[21] Appl. No.: 201,438

[22] Filed: Jun. 2, 1988

[51] Int. Cl.$^5$ .................. C07H 5/04; C07H 15/00; C08B 3/00; C08B 11/00
[52] U.S. Cl. .................. 536/18.7; 536/32; 536/43; 536/114; 536/17.2; 536/33; 536/31; 536/55.2; 530/350
[58] Field of Search .............. 536/18.7, 55.2, 31, 536/114, 33, 17.2, 32, 43; 530/350

[56] References Cited

U.S. PATENT DOCUMENTS

| | | | |
|---|---|---|---|
| 4,365,050 | 12/1982 | Ivani | 530/353 |
| 4,675,394 | 6/1987 | Solarek et al. | 536/14 |
| 4,683,298 | 7/1987 | Yalpani | 536/18.7 |

*Primary Examiner*—Ronald W. Griffin
*Assistant Examiner*—Everett White

[57] ABSTRACT

New amines and amides of carboxylated polysaccharides having the nitrogen of the amido and amino groups directly attached to the polysaccharides and method of making same, based on reacting in solution a material having carboxyl-containing polysaccharides, such as carboxymethyl cellulose, with ammonium donors having the general formula >NH such as primary and secondary amine reagents and with or without a reducing agent to obtain amides or amines. These products may be used for instance in biological separations, for the immobilization of proteins, for the removal of metal ions, as thickeners, and as suspension agents.

23 Claims, No Drawings

PROCESSES FOR THE PREPARATION OF AMIDES AND AMINES FROM A MATERIAL HAVING CARBOXYL-CONTAINING POLYSACCHARIDES AND PRODUCTS THEREFROM

This invention is directed to the amidation and amination of a material having carboxyl-containing polysaccharides and new amides and amines relating therefrom and to methods of using same.

BACKGROUND OF THE INVENTION

Polysaccharides are well known and are also referred to as glycans (carbohydrate or sugar polymers) which are made up of simple sugar units, and include cellulose, starch, chitin, dextran, glycogen as well as microbial and other types of polysaccharides. Encyclopedia of Polymer Science Vol 11, Interscience Publisher 1969, p.396 deals in some detail with the subject.

As far as direct and selective amidation or amination of polysaccharides is concerned, applicants have never found any reference teaching the amidation or amination target on carboxyl groups to obtain amines and amides having the nitrogen of the amines or amides directly attached to the polysaccharides.

THE INVENTION

Broadly stated, the invention is directed to a selective process for the amidation of a material having at least one carboxy-containing polysaccharide, comprising reacting in a solvent, a material having at least one carboxyl-containing polysaccharide with an ammonium donor having the general formula $>NH$, to convert the carboxyl groups of said carboxyl-containing polysaccharide, into amido groups. This invention thereby targets the amidation on specific sites by direct and selective amidation as opposed to the indirect amidation involving prior modifications of hydroxy groups.

The invention is also directed to the conversion of the carboxyl groups of carboxylated polysaccharides into amino groups by further adding a suitable reducing agent during at least a part of the amidation reaction. The amidation may also be carried out during at least a part of the amidation reaction, using a Hoffman type reaction to obtain the conversion of an unsubstituted amide to a primary amine with the loss of one carbon atom. This may be accomplished with an aqueous alkaline halogen reagent producing Hoffman reaction, such as alkaline bromine, alkaline chlorine, and hypochlorate. The most commonly preferred reagents being bromine and NaOH, or sodium hypochlorate (NaOCl). The amine products resulting therefrom are also new and useful as evidenced further on, and differ from the conventional amination involving hydroxy groups of the saccharide rings. The amides and amines so obtained may be referred to as amidogen, i.e. having the general formula $RCONHR_1$ or $RCH_2NHR_1$ or $RNHR_1$ wherein R is a polysaccharide back bone, and $R_1$ is an alkyl, alkene, alkyne, a carbohydrate, and alkyl having various substituted groups and cyclic and aromatic groups, as discussed hereinbelow with reference to the expression ammonium donor. These products may, for instance, be used in biological separations, as thickeners, as suspension agents and in many other applications.

The other ingredients, if any, forming the material having at least one carboxyl-containing polysaccharide may be any substance that does not cause steric hindrance or inhibition action of the amidation or if desired, the amination reaction.

By the expression carboxyl-containing polysaccharide is meant a material having a $-CO-O^-$ group or a precursor thereof. The $-CO-O^-$ group may be attached to a nitrogen group, such as $-NHCO_2^-$, or carbon group, such as $-C-CO_2^-$ or an oxygen group, such as $-O-CO_2^-$. The carboxyl group may be in the acid form such as COOH, and derivatives thereof, such as in the form of esters, or ionizable salts. Examples of the latter function include those of group 1 metals, such as Na, or group 2 metals, such as Ca.

By the expression ammonium donor is meant a product that has or is able to yield the general formula $>NH$ and includes amino compounds having a $>NH$ group, for instance: ammonia gas, ammonium hydroxide, inorganic or organic salts thereof, (such as ammonium salts of carboxylic acids, ammonium acetate, ammonium chloride), amines, polyamines, such as diamino compounds, amino alkyl sulfates, amino acids, including salts, and esters thereof, amino compounds having other functional groups not hindering the reaction, such as amino alcohols, aminothio compounds, aminoalkoxy alcohols, aminoalkyl sulfate, amides, acrylamides, alkylene amides, 2-(2-aminoethoxy) ethanol, cyclic amino compounds. The amino compound may comprise other groups such as alkanes, and unsaturated groups such as alkenes, alkynes, cyclic and aromatic groups, and ether groups, COOH, OH, halogen, thio-, phosphate functions and the like, as long as said groups do not cause steric hindrance or inhibiting action on the amidation, or if desired, the amination reaction. The other amines may be primary and secondary, and including other ammonium products, such as quaternary ammonium salts, amino sugars, such as chitosan, glucosamine hydrochloride, 2-aminoethyl hydrogen sulfate, and diethylaminoethyl chloride hydrochloride, polypeptides and proteins to produce in these last two instances, polypeptide and protein derivatives of carboxyl-containing polysaccharides.

The expression carboxyl-containing polysaccharide means for instance, carboxyl-containing polysaccharides in the form of celluloses, starches, chitins, chitosans, guar gums, glycans, galactans, glucans, xanthan gums, alginic acids, polymannuric acids, polyglycosuronic and polyguluronic acids, mannans, dextrins and cyclodextrins, as well as other synthetically carboxylated or naturally occuring carboxylated polysaccharides, which may be linear or branched. The polysaccharide may be a furonosan or pyranosan associated with proteins, lipids, or other molecules, and may include algal, plant, bacterial and mucopolysaccharides, glycogen, pectin, glycoproteins, and glycolipids, provided the polysaccharide has carboxyl-containing groups and is free from groups interfering in the amidation or the amination process.

The most commonly used solvent is an aqueous medium, but may also include organic solvents, such as dimethyl sulfoxide, dimethyl formamide, and dimethyl acetamide.

If an amine is desired, a suitable reducing agent may be used, such as for instance, sodium cyanoborohydride, sodium hypochloride, sodium hypobromide, and any reducing agent for amide groups to obtain amines. Other examples include catalytic hydrogenation, $LiAlH_4$, and sodium borohydride ($NaBH_4$).

THE PREFERRED WAY OF CARRYING THE INVENTION

The amidation being an equilibrium type reaction (as in the preparation of esters), it is preferable in order to obtain a stable product, to reduce the amide produced thereby shifting the equilibrium to increase the conversion yields. The amidation is generally carried out at ambient temperature. The polysaccharide is dissolved in water; the amount of water used, may for instance be that required to dissolve the polysaccharide and ammonium donor. The amount of ammonium donor being at least the equivalent amount required to react with the carboxyl group of the polysaccharide.

The amine product s obtained can be collected by freeze drying or by adding organic solvent, such as acetone or methanol to precipitate it out. (Also referred to as quenching).

EXAMPLES

The following examples will serve to illustrate particular embodiments of the invention.

EXAMPLES 1-5

Five cellulose aminoethylether derivatives were prepared in the following manner in each example: An aqueous solution of carboxymethyl cellulose sodium salt (Na CMC and also referred to as CMC or carboxymethyl cellulose), 0.8 to 2.0% w/v as described in Table 1, page 16, was treated with an aqueous solution of ammonium acetate ($CH_3COONH_4$), 0.44 to 10.0% w/v at room temperature, for periods between 5 to 10 days in the presence of an appropriate reducing agent, i.e. sodium cyanoborohydride ($NaBH_3CN$), 0.03 to 1.0% w/v. The resulting products showed nitrogen incorporation values of 1.17-3.53%, as shown in Table 1, page 16.

EXAMPLES 6-7

A reaction of Na CMC as described for Examples 5 and 3 respectively, for 5 days was performed and then the reducing reagent was added and the reaction was continued for another day. The results are shown in Table 1.

EXAMPLES 8-9

Carboxymethyl cellulose sodium salt was treated as in Examples 1-5, except that the reducing reagent was introduced 20 hrs after treatment of Na CMC with ammonium acetate. The reaction was carried out at ambient temperature for 3 to 8 days. The results are shown in Table 1.

EXAMPLES 10-11

The reaction of Na CMC as described for Examples 1-5 in the absence of a reducing reagent for periods of 5 to 10 days was carried out to produce the corresponding amide ether derivatives with nitrogen incorporations of 4.32-5.2% as shown in Table 1.

EXAMPLE 12

A reaction of Na CMC as described for Examples 1-5 was carried out in the presence of sodium cyanoborohydride as reducing agent at 75° C. for 5 days. The obtained results are shown in Table 1.

EXAMPLES 13-15

Reactions of carboxymethyl cellulose sodium salt (0.5-1.0% w/v) were carried out with glucosamine-hydrochloride (1.5-3.0% w/v) in the presence of equimolar amounts of base, such as a sodium bicarbonate solution (0.55-1.1% w/v) to neutralize the hydrochloride, sodium cyanoborohydride as hydride and as reducing reagent (0.27-0.50% w/v), at room temperature, producing 2-amino-2-deoxy-glucose derivatives of carboxymethyl cellulose with nitrogen incorporation values of 2.60-3.07%, as shown in Table 2, page 17.

EXAMPLE 16

A reaction of carboxymethyl cellulose with glucosamine hydrochloride was carried out as described for Examples 13-15, but under exclusion of light for 10 days, thereby producing 2-amino-2-deoxy-glucose derivatives of carboxymethyl cellulose with N-contents of 2.02%, as shown in Table 2.

EXAMPLES 17-18

Reactions of carboxymethyl cellulose with glucosamine hydrochloride were carried out as described for Examples 13-15, but with the addition of the reducing reagent 20 hrs after starting the reaction, to produce the corresponding amine derivatives having N-contents of 0.56-1.94%, as shown in Table 2.

EXAMPLE 19

The reaction of carboxymethyl cellulose with glucosamine hydrochloride as described for Examples 13-15, but at 60°-80° C. for 7 days to produce the corresponding amine with N-contents of 2.06%, as shown in Table 2.

EXAMPLE 20

The reaction of carboxymethyl cellulose with glucosamine hydrochloride was carried out as described for Example 13-15, in the presence of sodium hypochlorite as reducing reagent to produce the corresponding amine derivatives with N-contents of 0.3-0.52%, as shown in Table 2.

EXAMPLES 21-22

Reactions of carboxymethyl cellulose with glucosamine hydrochloride were carried out as described for Examples 13-15, in the absence of a reducing reagent at room temperatures, to produce the corresponding 2-amido-2-deoxy-glucose derivatives of carboxymethyl cellulose with N-contents of 0.05-0.06%, as shown in Table 2.

EXAMPLE 23

The reaction of carboxymethyl cellulose with glucosamine hydrochloride was carried out as described for Examples 21-22, but at higher temperature (50°-60° C.) to produce the corresponding amide derivatives with N-contents of 0.16%, as shown in Table 2.

EXAMPLES 24-25

The reaction for of carboxymethyl cellulose with 2-aminoethylhydrogen sulphate (0.64-1.4% w/v) was carried out 7-10 days at room temperature, in the presence of sodium hydrogen carbonate to obtain a basic medium and block the acidic function, yielding the corresponding amide derivatives with N-incorporation of 0.11–0.18% and S-incorporation of 0.52–1.18%, as shown in Table 3, page 18.

EXAMPLES 26–27

Reactions of carboxymethyl cellulose with beta-alanine in the presence of sodium hydrogen carbonate as described in Examples 24–25, gave the corresponding amide derivatives with N-contents of 0.12–0.37%, as shown in Table 3.

EXAMPLES 28–29

Reactions of carboxymethyl cellulose with 6-amino caproic acid in the presence of sodium hydrogen carbonate at room temperature were carried out as described for Examples 24–25, to produce the corresponding amide derivative with N-contents of 0.58%, as shown in Table 3.

EXAMPLE 30

The reaction of carboxymethyl cellulose with glycine methyl ester hydrochloride in the presence of sodium hydrogen carbonate was carried out as described for Examples 24–25, to produce the corresponding amide derivatives with N-contents of 0.65%, as shown in Table 3.

The products from Examples 24 to 30 have biological applications, such as in biological separations.

EXAMPLES 31–34

Carboxymethyl cellulose sodium salt was reacted with a bifunctional diamine reagent, (piperazine, 1,3-diaminopropane, iminopropylamine and 1,6-hexanediamine, respectively) at room temperature for 5–7 days to obtain the corresponding aminated carboxymethyl cellulose derivatives with N-contents of 5.25, 4.84, 6.34 and 4.81%, respectively as shown in Table 4, page 19, namely: carboxymethyl cellulose piperazine derivative, carboxymethyl cellulose 1,3-diaminopropane derivative, carboxymethyl cellulose iminobispropylamine derivative, and carboxymethyl cellulose 1,6-hexanediamine derivative. In such systems, cross-linking is possible as a result of using the bifunctional diamine reagents.

EXAMPLES 35–37

Reactions of carboxymethyl cellulose sodium salt with aliphatic amines or amides such as 1-amino-2-propanol, 2-(2-aminoethoxy)ethanol and acrylamide at room temperature were carried out for period of 5–7 days to produce the corresponding amine or amide derivatives with N-contents of 0.43–3.49%, as shown in Table 5, respectively: carboxymethyl cellulose 1-amino-2-propanol derivative, carboxymethyl cellulose 2-(2-aminoethoxy)ethanol derivative, and carboxymethyl cellulose acrylamide derivative.

EXAMPLE 38

To an aqueous solution of carboxymethyl cellulose sodium salt (10.0 gm/L) was added ammonium chloride ($NH_4Cl$, 100.0 gm) followed by sodium cyanoborohydride (10.0 gm). Concentrated hydrochloric acid (3.0 ml) was added to adjust the pH to 3 and the mixture was stirred at room temperature for two days. At that time another portion of ammonium chloride (100.0 gm) was introduced and the pH was adjusted to 2. At the end of reaction time (6 days) the pH was found to be about 7. The product wa dialyzed and lyophilized to afford the corresponding amine hydrochloride derivative with N-content of 7.18% and Cl-content of 8.92%.

EXAMPLES 39–41

Carboxymethyl cellulose sodium salt (low viscosity; 1.0% w/v) was treated with ammonia gas in the presence of a reducing agent (sodium cyanoborohydride, 0.03% w/v) at room temperature. Products were obtained after 1, 2 and 3 hrs (called Examples 39, 40 and 41) and the reaction mixture was stirred under the same conditions for another 24 hrs. The products were dialyzed and lyophilized to produce the corresponding amines with N-contents of 0.79–1.09%, as shown in Table 6, under Examples 39, 40 and 41.

EXAMPLE 42

Part of the product solution obtained in Example 41 was stirred at room temperature for 30 minutes, then quenched with methanol followed by dialysis and lyophilization to produce the corresponding (amide confirmed on IR analysis) with N-contents 1.86–1.93%, as shown in Table 1.

EXAMPLES 43–44

Carboxymethyl cellulose sodium salt, medium viscosity, was treated under the same conditions as described for Examples 39–41. The amine derivatives obtained after 2 and 4 hrs showed N-contents of 1.76 and 2.49%, respectively, as shown in Table 6.

EXAMPLE 45

Aminated carboxymethyl cellulose obtained as described in Example 2 was treated with hydrophilic residues such as maltose hydrate (0.04% w/v) in the presence of sodium hypochlorite as reducing agent (0.05% w/v) for 4 days at room temperature, to produce the corresponding branched aminated carboxymethyl cellulose derivatives with N-contents of 0.63–0.85%.

EXAMPLES 46–50

Low viscosity carboxymethyl cellulose (0.01% w/v) was treated with ammonia gas in the presence of $NaBH_3CN$ (0.03% w/v) for 1.5 hrs at room temperature. At that time two samples were taken (Examples 46–47). The first sample was quenched immediately with methanol to produce the amide derivative with N-contents of 1.54%. The second sample was stirred under the same conditions for 7 days to produce the corresponding amine with N-contents of 0.89%. The remaining solution was reacted in situ with a hydrophilic residue (respectively, xylose, maltose and dextrin in three different experiments) to produce the corresponding branched aminated carboxymethyl cellulose derivatives with N-contents 0.66–1.0%, as shown in Table 7, namely: aminocarboxymethy cellulose (1-deoxyxylit-1-yl) ether, aminocarboxymethyl cellulose (1-deoxymaltit-1-yl) ether, and aminocarboxymethyl cellulose (1-deoxy-dextrit-1-yl) ether respectively, the amine group reacting with the aldehyde in position 1 of the carbohydrate.

EXAMPLES 51–55

Medium viscosity carboxymethyl cellulose was treated as described for Examples 46–50. The results are shown in Table 7.

EXAMPLES 56–57

Aminated carboxymethyl cellulose obtained as described in Example 34 was coupled with proteins such as trypsin (type II, Sigma, T-8128) in aqueous solution in the presence or absence of coupling reagents such as 1-ethyl-3-(3-dimethyl aminopropyl) carbodiimide hydrochloride and sodium cyanoborohydride as reductive alkylation reagent to produce the corresponding trypsin conjugate of carboxymethyl cellulose, which showed N-contents of 2.95 and 1.68%, respectively, as shown in Table 8.

EXAMPLES 58-59

Aminated carboxymethyl cellulose obtained a described in Example 43 was treated with insulin (from Bovine pancreas, Sigma, I-5500) as described in Examples 56-57 to produce the corresponding insulin-carboxymethyl cellulose conjugates that showed N-contents of 6.09 and 6.39%, as shown in Table 8.

EXAMPLES 60-61

Aminated carboxymethyl cellulose obtained as described in Example 39 was treated with human albumin (Sigma, A-9511) as described in Examples 56-57 produce the corresponding albumin-carboxymethyl cellulose conjugates which showed N-contents of 6.38 and 5.52%, as shown in Table 8.

EXAMPLE 62

Aminated carboxymethyl cellulose derivatives ($4 \times 10^{-3}$% w/v) obtained as described in Examples 40 and 44 were treated with copper sulfate (50 ml, 1000 ppm) for 16 hrs at room temperature. The copper complex was isolated by dialysis and lyophilized to obtain the corresponding copper aminated carboxymethyl cellulose complex. Copper capacities of 1.6 and 1.8 mmol/gm were obtained, respectively thereby illustrating a method for removal of metal ions from aqueous solutions containing metal ions.

OTHER WAY OF CARRYING OUT THE INVENTION

Although the invention has bee disclosed with material comprising carboxyl-containing polysaccharides, the invention can be carried out with material comprising only part of said carboxyl-containing polysaccharides. The other portion being made up of substances not interferring with the amidation, and when contemplated, the amidation as contemplated herein.

EXAMPLE 63

Aminated Xanthan Gum

Xanthan gum (0.01% w/v) was treated with ammonia gas in the presence of a reducing agent (such as sodium cyanoborohydride, $2.9 \times 10^{-3}$% w/v) as described in Examples 39-41. Samples were obtained after 2.5, 6.0 and 24 hrs. The obtained aminated xanthan gum showed N-contents of 0.61; 0.71 and 1.42% respectively.

Having described the invention, modifications will be evident to those skilled in the art without departing from the spirit of the invention, as defined in the appended claims.

TABLE 1

AMINATION AND AMIDATION OF CARBOXYMETHYL CELLULOSE SODIUM SALT WITH AMMONIUM ACETATE

| Example | $CH_3COONH_4$ (% w/v) | Na CMC (% w/v) | $CH_3COONH_4$ Na CMC | Reaction Period (Days) | Reducing Agent $NaBH_3CN$ (% w/v) | Product N-Content[a] (%) |
|---|---|---|---|---|---|---|
| 1 | 0.44 | 0.8 | 0.55 | 10 | 0.44 | 1.17 |
| 2 | 6.6 | 2.0 | 3.3 | 5 | 0.03 | 2.5-3.20 |
| 3 | 10.0 | 1.0 | 10.0 | 5 | 0.75 | 2.7 |
| 4 | 10.0 | 0.5 | 20.0 | 7 | 0.37 | 3.53 |
| 5[b] | 5.0 | 1.0 | 20.0 | 5 | 1.0 | 3.25 |
| 6 | 5.0 | 0.25 | 20.0 | 6 | 0.01 | 4.22-4.88 |
| 7 | 10.0 | 1.0 | 10.0 | 6 | 0.37 | 4.18-2.69[c] |
| 8 | 1.0 | 2.0 | 0.5 | 3 | 1.0 | 1.79 |
| 9 | 1.0 | 2.0 | 0.5 | 8 | 1.0 | 1.31 |
| 10 | 5.0 | 0.25 | 20.0 | 5 | 0 | 4.90-5.22 |
| 11 | 5.0 | 0.25 | 20.0 | 10 | 0 | 4.32-4.50 |
| 10[d] | 10.0 | 1.0 | 10.0 | 5 | 0.69 | 3.19 |

[a] % w of N/w of N-Containing cellulose
[b] Ammonium acetate was added in two portions the second addition was introduced after 72 hrs.
[c] Sample was obtained after 5 days and before addition of $NaBH_3CN$.
[d] The reaction was carried out at 75° C.

TABLE 2

REACTION OF CARBOXYMETHYL CELLULOSE SODIUM SALT WITH D-GLUCOSAMINE HYDROCHLORIDE

| Example | Glucosamine HCl (% w/v) | Glucosamine HCl Na CMC (w/w) | Reaction Period (days) | Reducing Reagent (% w/v) | Sodium Bicarbonate (w/v) | Product N-Content (%) |
|---|---|---|---|---|---|---|
| 13 | 1.5 | 3.0 | 7 | 0.27 | 0.55 | 2.83 |
| 14 | 3.0 | 3.0 | 4 | 0.45 | 1.1 | 2.60 |
| 15 | 3.0 | 3.0 | 4 | 0.5 | 1.0 | 3.07 |
| 16 | 1.2 | 1.5 | 10 | 0.45 | 0.45 | 2.02 |
| 17 | 3.0 | 1.5 | 3 | 1.0 | 1.1 | 0.56 |
| 18 | 3.0 | 1.5 | 8 | 1.0 | 1.1 | 1.94 |
| 19 | 1.5 | 3.0 | 7 | 0.31 | 0.55 | 2.06 |
| 20 | 1.3 | 2.6 | 5 | 10.0 | satd. soln. | 0.3-0.52 |
| 21 | 1.3 | 2.6 | 5 | 0 | satd. soln. | 0.05-0.06 |
| 22 | 1.3 | 2.6 | 5 | 0 | satd. soln. | 0.05-0.06 |
| 23 | 1.3 | 2.6 | 3 | 0 | satd. soln. | 0.16 |

TABLE 3
REACTION OF CARBOXYMETHYL CELLULOSE SODIUM SALT WITH AMINO ACIDS AND AMINO ACID ESTER

| Example | Amino Acid or Ester | Amino Acid or Ester Conc. (% w/v) | Aminoacid or Ester Na CMC | Reaction Period (days) | $NaHCO_3$ (% w/v) | Product N-Content (%) | Product S-Content (%) |
|---|---|---|---|---|---|---|---|
| 24 | 2-aminoethyl hydrogen sulphate $H_2NCH_2CH_2OSO_3H$ | 0.64 | 1.3 | 7 | 0.33 | 0.22 | 0.52 |
| 25 | | 1.4 | 2.8 | 10 | 0.70 | 0.18 | 1.18 |
| 26 | Beta-Alanine $H_2N\ CH_2CH_2COOH$ | 0.33 | 0.65 | 7 | 0.33 | 0.12 | — |
| 27 | | 0.9 | 1.7 | 10 | 0.59 | 0.37 | — |
| 28 | 6-amino caproic acid $H_2N(CH_2)_5COOH$ | | 0.5 | 1.1 | 7 | 0.33 | 0.00 |
| 29 | | 1.3 | 2.6 | 10 | 0.80 | 0.58 | — |
| 30 | Glycine methyl ester hydrochloride $H_2N.CH_2COOC_2H_5.HCl$ | | 10.0 | 10.0 | 7 | 6.5 | — |

TABLE 4
REACTION OF CARBOXYMETHYL CELLULOSE SODIUM SALT WITH BIFUNCTIONAL AMINATING REAGENTS

| Example | Aminating Reagent | Reagent Conc. (% w/v) | Aminating Reagent Na CMC | Reaction Period (days) | Product N-Content (%) |
|---|---|---|---|---|---|
| 31 | piperazine | 10.0 | 10.0 | 7 | 5.25 |
| 32 | 1,3-diaminopropane $H_2N\ (CH_2)_3NH_2$ | 5.0 | 5.0 | 7 | 4.84 |
| 33 | iminobispropylamine $NH\ [(CH_2)_3NH_2]_2$ | 3.1 | 3.1 | 7 | 6.34 |
| 34 | 1,6-hexanediamine $H_2N\ (CH_2)_6\ NH_2$ | 2.0 | 2.0 | 5 | 4.81 |

TABLE 5
REACTION OF CARBOXYMETHYL CELLULOSE SODIUM SALT WITH ALIPHATIC AMINES AND AMIDES

| Example | Aminating Reagent | Reagent Conc. (% w/v) | Aminating Reagent Na CMC | Reaction Period (days) | Reducing Reagent (% w/v) | Product N-Content (%) |
|---|---|---|---|---|---|---|
| 35 | 1-amino-2-propanol $H_2N-CH_2-CH(OH)-CH_3$ | 10.0 | 10.0 | 7 | 0.5 | 3.49 |
| 36 | 2-(2-aminoethoxy) ethanol $H_2N-CH_2CH_2-O-CH_2CH_2OH$ | 10.0 | 10.0 | 7 | 0.5 | 2.95 |
| 37 | Acrylamide $CH_2=CH-CO-NH_2$ | 2.0 | 2.0 | 5 | 0.0 | 0.43 |

TABLE 6
REACTION OF CARBOXYMETHYL CELLULOSE SODIUM SALT WITH AMMONIA GAS

| Example | Na CMC Conc. (% w/v) | Reaction Period (hrs) | $NaBH_3CN$ (% w/v) | Product N-Content (%) |
|---|---|---|---|---|
| (low viscosity) | | | | |
| 39 | 1.0 | 1.0 | 0.03 | 0.78–0.80 |
| 40 | 1.0 | 2.0 | 0.03 | 0.94–1.03 |
| 41 | 1.0 | 3.0 | 0.03 | 1.02–1.09 |
| 42 | 1.0 | 3.5 | 0 | 1.86–1.93[a] |
| (medium viscosity) | | | | |
| 43 | 1.0 | 2.0 | 0.03 | 1.76 |
| 44 | 1.0 | 24.0 | 0.03 | 2.49 |

[a] Amide Derivative.

TABLE 7
AMINATED AND BRANCHED AMINATED CARBOXYMETHYL CELLULOSE PRODUCTS

| Example | Hydrophilic Residue | Na CMC Conc. (% w/v) | Hydrophilic Residue Conc. (% w/v) | Reaction Period | $NaBH_3CN$ (% w/v) | Product N-Content (%) |
|---|---|---|---|---|---|---|
| Low Viscosity Na CMC | | | | | | |
| 46 | | 0.01 | | 1.5 hr | 0.03 | 1.54[a] |
| 47 | | | | 7 days | 0.03 | 0.89 |
| 48 | xylose | | 1.0 | 7 days | 0.03 | 0.97 |
| 49 | maltose | | 0.5 | 7 days | 0.03 | 1.00 |

TABLE 7-continued

AMINATED AND BRANCHED AMINATED CARBOXYMETHYL CELLULOSE PRODUCTS

| Example | Hydrophilic Residue | Na CMC Conc. (% w/v) | Hydrophilic Residue Conc. (% w/v) | Reaction Period | NaBH$_3$CN (% w/v) | Product N-Content (%) |
|---|---|---|---|---|---|---|
| 50 | hydrate dextrin white | | 1.0 | 7 days | 0.03 | 0.66 |
| Medium Viscosity Na CMC | | | | | | |
| 51 | | 0.01 | | 1.5 hr | 0.03 | 1.37[a] |
| 52 | | | | 7 days | 0.03 | 0.53 |
| 53 | xylose | | 1.0 | 7 days | 0.03 | 1.16 |
| 54 | maltose | | 0.5 | 7 days | 0.03 | 1.19 |
| 55 | hydrate dextrin white | | 1.0 | 7 days | 0.03 | 0.60 |

[a]Amide derivatives

TABLE 8

COUPLING OF AMINATED CARBOXYMETHYL CELLULOSE WITH PROTEINS

| EX. | Conc. of Aminated CMC (% w/v) | N-Contents of CMC (%) | C/N[a] of Aminated CMC | Conc. of Protein (% w/v) | N* | C/N[a] of Protein | Coupling Reagent Conc. (% w/v) | NaBH$_3$CN (% w/v) | N** | C/N[a] of Product |
|---|---|---|---|---|---|---|---|---|---|---|
| | Trypsin Conjugate | | | | | | | | | |
| 56 | 0.01 | 4.81 | 8.82 | 0.02 | 8.34 | 4.53 | 0 | 0.03 | 1.69 | 24.59 |
| 57 | 0.02 | 4.81 | 8.82 | 0.03 | 8.34 | 4.53 | 0.01 | 0.03 | 2.95 | 14.07 |
| | Insulin Conjugate | | | | | | | | | |
| 58 | 0.01 | 2.49 | 14.93 | 0.01 | 14.82 | 3.35 | 0 | 0.03 | 6.39 | 6.21 |
| 59 | 0.02 | 2.49 | 14.93 | 0.01 | 14.82 | 3.35 | 0.01 | 0.03 | 6.09 | 7.21 |
| | Albumin Conjugate | | | | | | | | | |
| 60 | 0.01 | 0.80 | 48.60 | 0.01 | 15.32 | 3.25 | 0 | 0.02 | 5.52 | 7.33 |
| 61 | 0.02 | 0.80 | 48.60 | 0.01 | 15.32 | 3.25 | 0.01 | 0.02 | 6.38 | 6.76 |

[a]C/N is carbon/nitrogen ratio.
*N-Contents of Protein
**N-Contents of Product

We claim:

1. An amidogen of a carboxyl-containing polysaccharide selected from the group consisting of amido alkyl ether and amino alkyl ether of carboxyl-containing polysaccharides,
wherein the nitrogen of the amido and amino group is directly attached to an alkyl group, said alkyl group itself joining an oxygen and said oxygen joining a carbon forming (a) one (poly)saccharide ring unit of said carboxyl-containing polysaccharide, at either:
(a) position 5 or
(b) at least one of the positions 2, 3 and 6 of said saccharide ring,
said group selected from amino alkyl ether and amino alkyl ether defining in the case of (b) a side chain that is exocyclic of said polysaccharide ring, and in the case of (a) of amino alkyl and amino alkyl directly attached to the carbon of the position 5 of a polysaccharide unit,
and in the case of (a), carboxyl groups being present on position 5 of saccharide ring units of said carboxyl-containing polysaccharide, and in the case of (b), alkyl carboxyl groups being present in at least one of the positions 2, 3 and 6 of saccharide ring units of said carboxyl-containing polysaccharide.

2. The amido polysaccharide as defined in claim 1 being cellulose amidomethylether obtained from the amidation of carboxymethyl cellulose.

3. The cellulose amidomethylether as defined in claim 2 having a N-content in % by weight of about 4 to 5.3%.

4. The amido polysaccharide as defined in claim 1 being a cross-linked amido polysaccharide.

5. The amido polysaccharide as defined in claim 4 wherein said cross-linking is obtained with a diamino compound.

6. The amido polysaccharide as defined in claim 1 being an amido alkyl sulphate.

7. The amido polysaccharide as defined in claim 1 being an amido acid polysaccharide.

8. The amido acid polysaccharide as defined in claim 7, being an amido alkyl sulfate polysaccharide.

9. The amido acid polysaccharide as defined in claim 1 being an amido thio polysaccharide.

10. The amido acid polysaccharide as defined in claim 1 being an amido sugar polysaccharide.

11. The amido polysaccharide as defined in claim 1 being a 2-amido-2-deoxy-glucose derivative of carboxymethyl cellulose.

12. The amido polysaccharide as defined in claim 1 being an amido alcohol.

13. The amido polysaccharide as defined in claim 1 being cellulose amidomethylether.

14. The amido polysaccharide as defined in claim 1 being an amido amino alkyl derivative of carboxymethyl cellulose.

15. The amido polysaccharide as defined in claim 1 being an amido amino aryl derivative of carboxymethyl cellulose.

16. The amidogen polysaccharide as defined in claim 1 being selected from the group consisting of: carboxymethyl cellulose piperazine derivative, carboxymethyl cellulose 1,3-diamino propane derivative,
carboxymethyl cellulose iminobispropylamine derivative,
carboxymethyl cellulose 1,6-hexanediamine derivative,
carboxymethyl cellulose 1-amino-2-propanol derivative,
carboxymethyl cellulose 2-(2-aminoethoxyethanol) derivative,
carboxymethyl cellulose acrylamide derivative,
aminocarboxymethyl cellulose (1-deoxyxylit-1-yl) ether,
aminocarboxymethyl cellulose (1-deoxymaltit-1-yl) ether, and,
aminocarboxymethyl cellulose (1-deoxy-dextrit-1-yl) ether.

17. The amidogen polysaccharide as defined in claim 1 being aminated carboxymethyl cellulose.

18. The aminated carboxymethyl cellulose as defined in claim 17 being cellulose amidomethylether having a N-content in % by weight of between 1 to 5%.

19. The amidogen polysaccharide as defined in claim 1 being a 2-amino-2-deoxy-glucose derivative of carboxymethyl cellulose.

20. The 2-amino-2-deoxy-glucose derivative of carboxymethyl cellulose as defined in claim 19 having a N-content of 1.9% to 3.1%.

21. The amidogen polysaccharide as defined in claim 1 being a member selected from protein-carboxymethyl cellulose conjugates and polypeptide carboxymethyl cellulose conjugates.

22. The amidogen polysaccharide as defined in claim 1 being selected from the group consisting of:
trypsin carboxymethyl cellulose, and
albumin carboxymethyl cellulose and insulin carboxymethyl cellulose conjugates.

23. The amidogen polysaccharide as defined in claim 1 being an aminated xanthan gum.

* * * * *